(12) United States Patent
Wnek et al.

(10) Patent No.: US 8,497,408 B2
(45) Date of Patent: Jul. 30, 2013

(54) TREATMENT FOR HIGH PRESSURE BLEEDING

(75) Inventors: Gary Wnek, Midlothian, VA (US); Marcus E. Carr, Jr., Richmond, VA (US); Gary Bowlin, Mechanicsville, VA (US); Kelman I. Cohen, Richmond, VA (US); Kevin R. Ward, Glenn Allen, VA (US); Wayne Barbee, Glen Allen, VA (US); Rao Ivatury, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 1327 days.

(21) Appl. No.: 11/855,205

(22) Filed: Sep. 14, 2007

(65) Prior Publication Data

US 2008/0009898 A1      Jan. 10, 2008

Related U.S. Application Data

(62) Division of application No. 10/363,994, filed as application No. PCT/US01/28295 on Sep. 12, 2001, now abandoned.

(60) Provisional application No. 60/231,883, filed on Sep. 12, 2000.

(51) Int. Cl.
*A61F 13/00* (2006.01)

(52) U.S. Cl.
USPC .............. 602/56; 602/42; 602/48; 602/53; 602/58

(58) Field of Classification Search
USPC .................... 602/42, 48, 53, 56, 58
See application file for complete search history.

(56) References Cited

U.S. PATENT DOCUMENTS

| | | | | |
|---|---|---|---|---|
| 3,670,731 A * | 6/1972 | Harmon | | 604/368 |
| 4,423,101 A | 12/1983 | Willstead | | 428/76 |
| 4,565,663 A | 1/1986 | Errede et al. | | 264/120 |
| 4,590,227 A | 5/1986 | Nakamura et al. | | 523/130 |
| 4,820,293 A | 4/1989 | Kamme | | 604/368 |
| 5,998,032 A | 12/1999 | Hansen et al. | | 428/403 |
| 6,054,122 A | 4/2000 | MacPhee et al. | | |
| 6,056,970 A | 5/2000 | Greenawalt et al. | | 424/426 |
| 6,066,325 A | 5/2000 | Wallace et al. | | |
| 6,106,913 A | 8/2000 | Scardino et al. | | 428/36.3 |
| 6,296,657 B1 | 10/2001 | Brucker | | 606/213 |

FOREIGN PATENT DOCUMENTS

| | | |
|---|---|---|
| WO | WO 98/44963 | 10/1998 |
| WO | WO 01/15754 A1 | 8/2000 |
| WO | WO 02/18441 A2 | 9/2001 |

OTHER PUBLICATIONS

Supplementary European Search Report, issed by the European Patent Office on Apr. 20, 2007, pp. 1 to 2.
Reneker et al., Nanometre DIameter Fibers of Ploymer, Produced by Electrospinning, Nanotechnology 7 (1996), pp. 216-223.
Doshi et al., "Electrospinning Process and Application of Electrospun Fubers", Jprunatl of Electrostatics, 35 (1995) 151-160.
Boland et al., Tailoring Tissue Engineering Scaffolds Using Electrostatic Processing Techniques: a Stady of Ply(Glycolic Acid) Electrospinning, J. Mcromol. Sci. Pure Appl. Chem, A38(12), 1231-1243(2001).

* cited by examiner

*Primary Examiner* — Ali Soroush
(74) *Attorney, Agent, or Firm* — Whitham Curtis Christofferson & Cook, PC

(57) ABSTRACT

High-pressure bleeding wounds (and other bleeding wounds) may be treated by applying direct pressure directly in the bleeding wound, such as by applying a back pressure in a confined space around and in the wound. Certain substances and articles may be inserted into the wound, and the wound may be enclosed with that substance or article (such as a hemostatic substance, which may be polymeric), by swelling on contact with molecules (such as water molecules in the blood) encountered in the wound, generates the desired pressure to stop or at least reduce the bleeding without the detrimental effects of a tourniquet. Clot-inducing substances may be introduced into the wound contemporaneously with direct pressure application directly in the wound. Compressible and non-compressible wounds are treated. Treatment stops bleeding without producing pressure injury or ischemic damage. Medical devices using this technology are provided, including removable, biodegradable, medic-administrable devices.

4 Claims, 16 Drawing Sheets

SEM OF EVA ELECTROSPUN MAT

ETHYLENE VINYL ACETATE - EVA

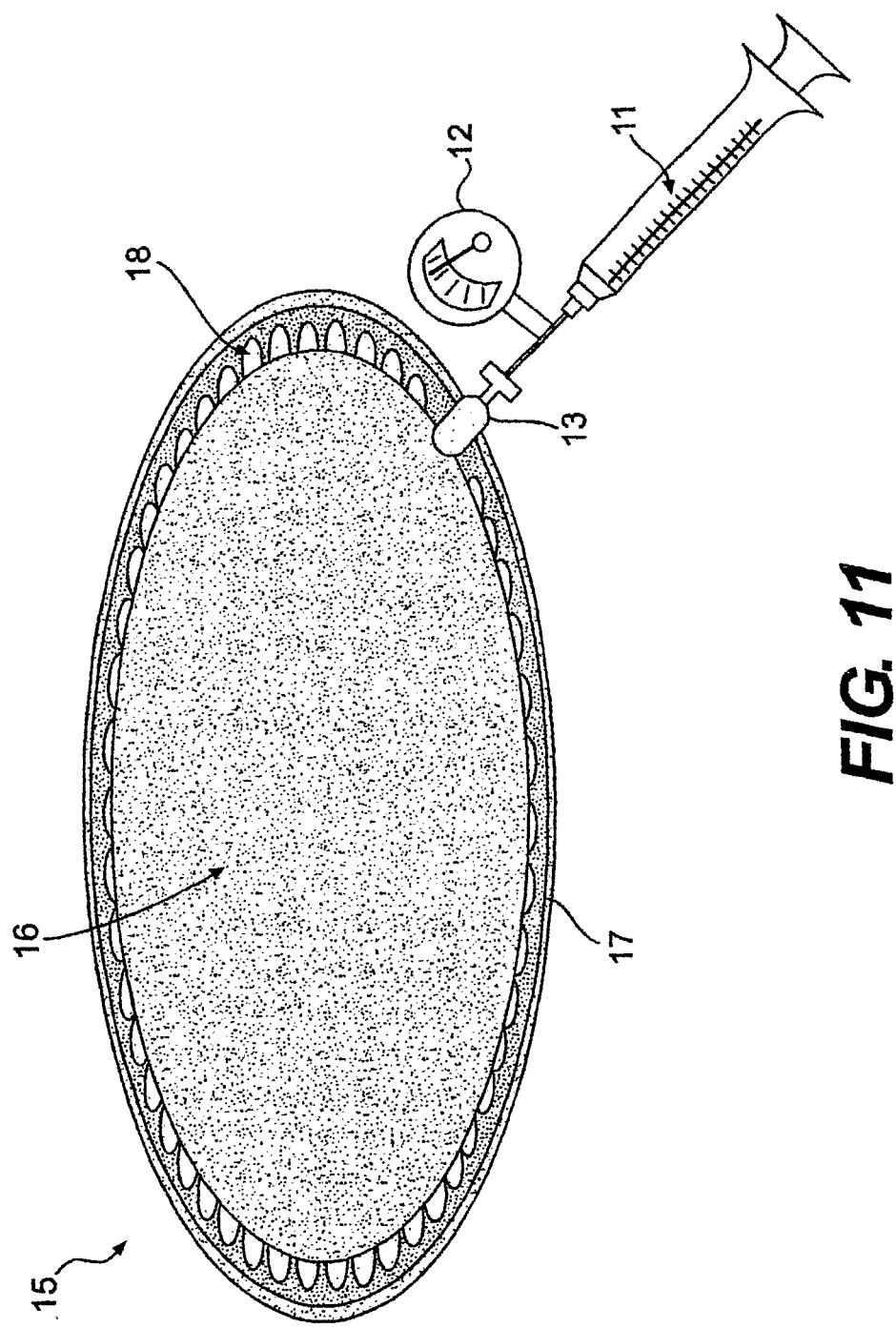

TREATMENT FOR HIGH PRESSURE BLEEDING

CROSS-REFERENCE TO RELATED APPLICATIONS

This application is a divisional of U.S. patent application Ser. No. 10/363,994, filed Aug. 13, 2003 now abandoned which itself claims priority to PCT/US01/28295 filed Sep. 12, 2001 and U.S. Provisional 60/231,883 filed Sep. 12, 2000, and the complete contents of these applications is herein incorporated by reference.

BACKGROUND OF THE INVENTION

1. Field of the Invention

The invention is generally related to emergency medicine. In particular, the invention relates to bleeding and bleeding injuries.

2. Background Description

The morbidity and mortality from penetrating injuries (such as ballistic injuries in combat, knife wounds, penetrating wounds secondary to motor vehicle accidents, etc.) has decreased over the past fifty years. However, some undesirable results remain. Present treatments for high pressure, i.e. arterial, bleeding can cause ischemia that might contribute to limb loss. Tourniquet use can contribute to the need for amputation. This is especially true if there is a significant delay in definitive treatment.

As to military trauma, two characteristics of death due to such trauma are seen. First, early death occurs. Soldiers who die due to injury, die early: about 40% die immediately; 25% die within 5 minutes; 15% die within 15 minutes; i.e., a total of 80% dead in the first 15 minutes after trauma. A second feature of military trauma is death due to bleeding, with ⅔ of military deaths due to trauma being due to hemorrhage.

Ballistic injury is a primary mode of trauma in combat. Such injuries can be associated with rapid blood loss due to vascular disruption. In the Vietnam conflict, ten percent of wounds to the extremity were associated with major artery injury. M. E. Jabaley, H. D. Peterson, "Early treatment of war wounds of the hand and forearm in Vietnam," Ann Surg 1973; 177:167-73. While bleeding from compressible vessels may respond to direct pressure, blood loss from deep muscular branches (such as those from the profunda femoris artery, etc., e.g., see Table 1) may be severe. S. M. Henry, R. Tornetta III, T. M. Scalea, "Damage control for devastating pelvic and extremity injuries," Surg Clin North Am, 77:879-95 (1997). Despite increasingly aggressive surgical treatment, limb salvage has not improved. P. V. Sharma, S. C. Babu, P. M. Shah, R. H. Clauss, "Changing patterns in civilian arterial injuries," J. Caridovasc Surg (Torino), 26:7-11 (1985). Death from hemorrhagic shock remains a problem even in very healthy individuals. J. Valentine, S. Blocker, J. H. Chang, "Gunshot injuries in children," J Trauma, 24:952-6 (1984). As can be appreciated from the following Table 1, combat vascular injuries continue to result in a 12 to 30 percent amputation rate depending on the involved vessel.

TABLE 1

(Incidence of major lower extremity vascular injuries in the three great wars) (Source: Vascular Trauma, Rich N. M. and Spencer, F. C. (eds.), W. B. Sunders, Philadelphia, 1978).

| War | Total Arteries | Common Iliac | External Iliac | Common femoral | Deep Femoral | Superficial Femoral | Popliteal |
|---|---|---|---|---|---|---|---|
| WWI | 1202 | 1 | 4 | | | 366 | 144 |
| WWII | 2471 | 13 | 30 | 106** | 23 | 517 | 502 |
| Korean | 304 | | | | | 95! | 79# |
| Vietnam | 1000 | 9 | 17* | 46*** | | 305@ | 217# |

*three amputations and one death
**ligation lead to 86 amputations
!12% amputation rate
***15% amputation rate, 3 deaths
@37 amputations or 12.1%
30% amputation rate Nor is the high incidence of deaths and amputations from penetrating wounds only for combat injuries. Treatment of trauma also is important in the civilian arena. At one Level I civilian trauma center in Virginia, from 1995 to 1999, of 66 patients with penetrating extremity vascular injuries, there were five deaths from hemorrhagic shock. Trauma is the most frequent cause of death in the United States in persons under the age of 34. Because trauma occurs most in young people, trauma is the leading cause of life years lost. Up to 80% of all early trauma deaths are from uncontrolled hemorrhage. Each year in the United States, 1 in 100 people will visit an emergency room; 1 in 1000 people will be admitted and transfused; 1 in 3000 will die of trauma. About 50% of civilian deaths due to trauma are secondary to hemorrhage.

Currently available modalities for treating high pressure bleeding include tourniquets, fibrin glue, etc. However, these current bleeding treatments have significant disadvantages, such as nerve damage, limb ischemia, increased risk of amputation, etc.

Tourniquets were described more than two millenia (2000 years) ago as an adjuvant to surgical amputation. L. Zimmerman, I. Veith, *Great Ideas in the History of Surgery*, San Francisco, Calif.: Norman Publishing (1993), 31. Since then, tourniquets have become a primary a primary initial treatment for injuries associated with high pressure bleeding. Unfortunately, tourniquet use is associated with a variety of complications and difficulties including nerve damage, post-tourniquet syndrome, limb ischemia (distal ischemia), compartment syndromes, pulmonary embolus, increased risk of amputation, and limb wastage. A. K. Palmer, "Complications from tourniquet use," Hand Clinics, 2:301-5 (1986); A. S. Estrera, R. P. King, M. R. Platt, "Massive pulmonary embolism: a complication of the technique of tourniquet ischemia," J Trauma, 22:60-2 (1982). To decrease these risks, tourniquets must be intermittently loosened. This typically restarts the bleeding and is difficult for treating personnel to accomplish. Despite the potential complications and drawbacks, recent combat (such as the 1991-92 Croatian conflict) has verified the ability of tourniquets to delay shock in lower extremity arterial injuries. Z Lovric, V Lehner, B Wertheimer, L Kosic-Lovric, "Tourniquet occlusion technique for lower extremity artery reconstruction in war wound," J Cardiovasc Surg (Torino), 38:153-5 (1997).

While fibrin products (such as fibrin glue, fibrin sealant and dry fibrin dressing) have been developed and shown to be effective in stopping venous bleeding, such fibrin products do have drawbacks. Fibrin products have had a tendency to be washed from the wound during high pressure bleeding, relative high cost. Some fibrin products put the patient at risk of viral exposure. Virally inactivated fibrin sealant has been developed, and is being used as an adjuvant to multiple types of surgery. C J Dunn, K L Goa, "Fibrin sealant: a review of its use in surgery and endoscopy," Drugs, 58:863-86 (1999); M R Jackson, B M Alving, "Fibrin sealant in preclinical and clinical studies," Curr Opin Hematol, 6:415-9 (1999). Fibrin glue has been shown to be effective in speeding hemostasis along vascular graft suture lines. A A Milne, W G Murphy, S J Reading, C V Ruckley, "A randomised trial of fibrin sealant in peripheral vascular surgery," Vox Sang, 70:210-2 (1996). Fibrin glue has been tested as an adjuvant to surgery in the treatment of complex hepatic injury. S M Cohn, J H Cross, M E Ivy, A J Feinstein, M A Samotowka, "Fibrin glue terminates massive bleeding after complex hepatic injury," J Trauma, 45:666-72 (1998). Formulations of fibrinogen and thrombin containing dressings, and dry fibrin sealant dressings have been proposed and studied in pig models of vascular injury and grade V liver injury. M J Larson, J C Bowersox, R C Lim, Jr., J R Hess, "Efficacy of a fibrin hemostatic bandage in controlling hemorrhage from experimental arterial injuries," Arch Surg, 130:420-2 (1995); J B Holcomb, A E Pusateri, R A Harris, N C Charles, R R Gomez, J P Cole, L D Beall, V Bayer, M J MacPhee, J R Hess, "Effect of dry fibrin sealant dressings versus gauze packing on blood loss in grade V liver injuries in resuscitated swine," J Trauma, 46:49-57 (1999); J B Holcomb, A E Pusater, R A Harris, T J Reid, L D Beall, J R Hess, M J MacPhee, "Dry fibrin sealant dressing reduce blood loss, resuscitation volume, and improve survival in hypothermic coagulopathic swine with grade V liver injuries," J Trauma, 47:233-40 (1999). Dry fibrin sealant dressing was recently shown to be more effective than standard gauze in decreasing bleeding and maintaining blood pressure in ballistic injury. J Holcomb, M MacPhee, S Hetz, R Harris, A Pusateri "Efficacy of a dry fibrin sealant dressing for hemorrhage control after ballistic injury," Arch Surg, 133:32-5 (1998).

While the development of "dry" products has increased their potential as alternatives to tourniquets for battlefield treatment, several potential problems remain. First, these products are relatively expensive because they are made from human blood (requiring a large amount of starting materials and multiple purification processes). Second, although virally inactivated, the fibrinogen contained in the products comes from multiple human donors and cannot be considered totally safe in terms of viral transmission. Third, these products must be held in place until bleeding stops or the material may simply wash out of the wound. The wash-out problem is especially seen when the bleeding is brisk as with arterial involvement.

Thrombin-mediated polymerization of fibrinogen has been the staple of hemostat technology for decades. "Hemostatic" means anything with the ability to enhance, speed or support blood clotting. Indeed, a recent patent dealing with hemostat systems still focuses on this process. J J Prior, D G Wallace, D H Sierra, F A DeLustro, "Compositions containing thrombin and microfibrillar nanometer collagen, and methods for preparation and use thereof," U.S. Pat. No. 6,096,309 (2000).

Also, treatment of bleeding external wounds also has not progressed much, with conventional treatments not offering much beyond simply covering the wound. Most conventional dressings do little or nothing to promote hemostatis, prevent infection or relieve pain. Current bandages do little more than cover the wound and absorb fluids. There are emerging products that aid in hemostasis (fibrin glue, fibrin sealant, dry fibrin, kitosan, etc.) but most are quite expensive and some carry a risk of viral infection.

Another difficulty of conventional treatments for bleeding is that the patient loses much of his or her own blood, and transfusion is needed. Blood transfusion suffers from availability problems, purity concerns, etc., and is expensive. Costs of civilian blood transfusion for trauma were about $½ billion in 1997.

None of the current technologies adequately address the problem of treating high pressure arterial bleeding. A tourniquet alternative that is effective, inexpensive, lacks viral risk, and can be easily administered (such as by an army medic) would be a medical advance. A solution is still sought to the problem of assuring hemostatis and homeostasis for a penetrating injury (such as high-pressure bleeding combat wound) until the patient (such as a soldier) can reach a hospital facility for definitive care. Additionally, better treatment of bleeding external wounds is timely. Overall, better treatment of hemorrhage by the first responder would save lives, money and limbs, in military and civilian situations.

SUMMARY OF THE INVENTION

Leakage (such as bleeding) may be stopped or reduced relatively quickly by pressure equalization comprising enclosing a region around the leak and applying direct-pressure in or around the leak. Notably, bleeding (especially high-pressure bleeding from penetrating injuries such as combat wounds) may be treated by applying direct pressure within the wound, especially by enclosing an area around the wound and applying direct pressure in that enclosed area. Such direct-pressure application advantageously may be by a simple medical device (such as a device administrable by a medic). An inventive medical device may be placed directly in the wound, where it stops high pressure bleeding. The acute dressing is both removable for a definitive treatment, and biodegradable if not removed (such as because removal is not warranted). The inventive device is simple, easy to apply, much less expensive than other biological products, and does not expose the patient to viral contaminants. The invention directly addresses the problem of high pressure by simulating the time honored treatment of direct pressure, particularly, pressure directly within the wound.

The invention is particularly practical, in that four topics (topics 1a, 1c, 1f, 1g) of the nine research topics proposed in the hemorrhage control section of the Research on Combat Casualty Care program are addressed. The inventive medical devices and methods may be used in compressible (topic 1f) and non-compressible (topic 1a) bleeding. Medical devices and methods according to the invention are suitable for replacing the tourniquet as the primary field hemostat used by the medic (topic 1c). Because medical devices and treatment methods according to the invention are designed to avoid the ischemia associated with tourniquet use, they have no time limit on emergent use (topic 1g). Advantageously, the invention provides acute dressings and other medical devices that may be removed for definitive treatment while also being biodegradable if not removed.

Advantageously, the present invention moves away from the conventional treatment paradigm for penetrating high-pressure bleeding injuries of "first save the patient, then spare the limb" to a new paradigm of "save the patient and spare the limb."

In order to accomplish these and other objects of the invention, in a first preferred embodiment, the invention provides a method of treating a fluid leak (such as a bleeding wound), comprising inserting into the fluid leak a material swellable on contact with the leaking fluid.

In a second preferred embodiment, the invention provides a method of treating a bleeding wound, comprising applying direct pressure directly in the bleeding wound. Particularly preferred is to place directly in the wound a substance that swells at a rate of 100 to 300% volume increase per minute. Most preferably, direct pressure application continues until bleeding stops.

In a third preferred embodiment, the invention provides a medical device comprising a hemostatic substance placeable directly in a bleeding wound, wherein the wound is a compressible wound or a non-compressible wound. Advantageously, the invention provides devices that may be removable and/or biodegradable; devices that when placed in a bleeding wound swells at a rate of about 100 to 300% volume increase per minute; devices that produce pressure of greater than about 60 mm Hg in a confined space; devices administrable by a medic, etc.

Some aspects and features of the invention are now mentioned, without the invention being limited thereto.

The inventive methods and devices in an especially preferred embodiment may include applying a back pressure in a confined space around and in the wound. In another especially preferred embodiment, the invention may include inserting a direct-pressure-applying substance or article into the wound and enclosing the wound with the direct-pressure-applying substance or article therein. In a further especially preferred embodiment, the invention may include inserting a hemostatic substance or article into the wound and enclosing the wound (such as by placing a dressing over the wound) with the hemostatic substance or article therein.

Where the invention uses a hemostatic substance or article, in a particularly preferred embodiment, the hemostatic substance or article includes polymer fibers of diameter about 1 micron or less. In another particularly preferred inventive embodiment in which a hemostatic substance or article is used, the hemostatic substance or article swells upon contact with water molecules (such as water molecules contained in blood leaving the wound). Where a hemostatic substance or article is used, the hemostatic substance or article may be lightly crosslinked. Where a hemostatic substance is used, in a particularly preferred embodiment of the invention, the hemostatic substance swells from an initial volume to a 10-fold volume in one minute in a liquid; and/or the hemostatic substance generates at least 60 mm Hg pressure within three minutes of being placed in a bleeding wound.

In a particularly preferred embodiment of the invention, a membrane or shell encloses the swellable material, hemostatic substance or article, or the like. Most preferably, the membrane or shell stiffens as the interior hemostatic substance or article or swellable material swells.

The invention in a particularly preferred embodiment provides for using (such as placing in a wound or disposing in a device) a polymeric substance, such as a polymeric substance that is a microporous, hydrogel-forming polymer with rapid swelling kinetics. Preferably, the polymeric substance may be poly(acrylamide), hydroxypropyl cellulose, or a hydrophilic material.

The invention in a particularly preferred embodiment provides for placing a clot-inducing substance (such as thrombin, batroxobin, reptilase, a fibrinogen activating enzyme, etc.) in a wound to be treated.

DETAILED DESCRIPTION OF THE DRAWINGS

Figure 6A:
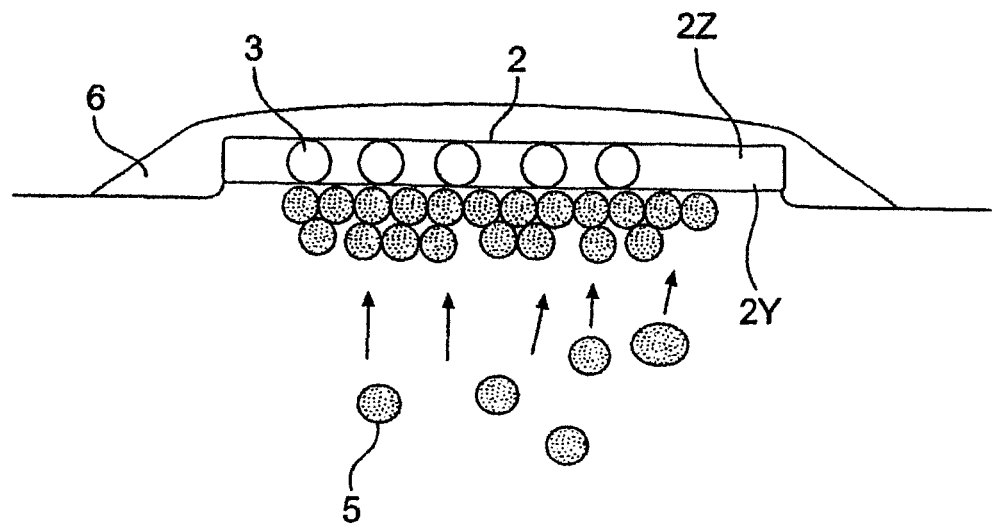
Figure 6B:
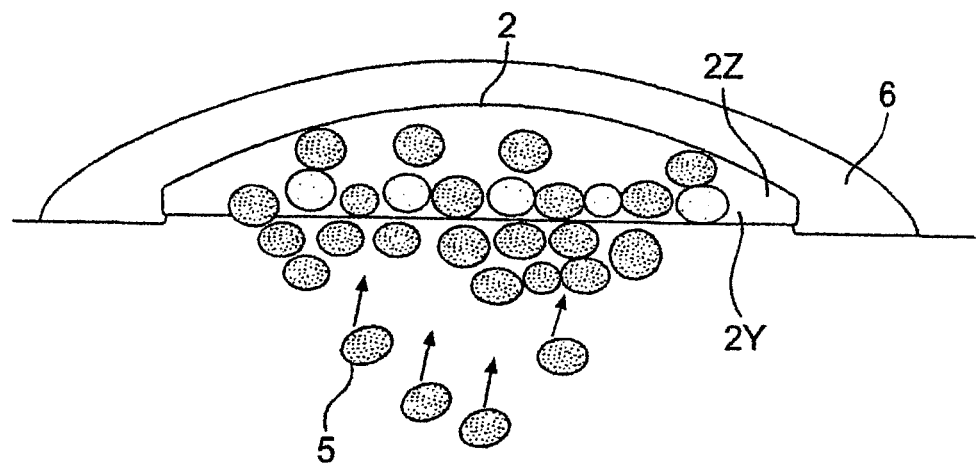
Figure 6C:
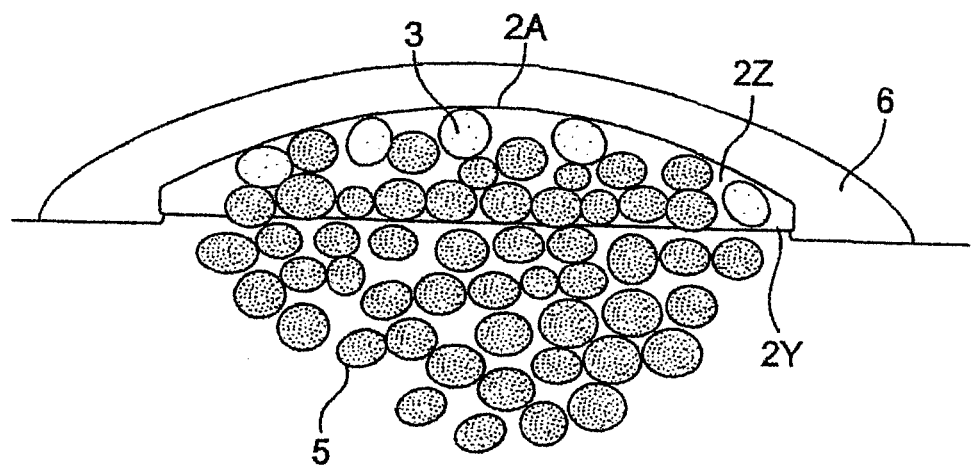

FIGS. 6A-C are representational drawings of the invention at a molecular-level in use treating a bleeding wound, including FIG. 6A where a fresh inventive device has been placed at a wound to be treated; FIG. 6B where the device has been in contact with the bleeding wound for a time; and FIG. 6C where the device has been in contact with the bleeding wound for a sufficient time to equalize pressure.

Figure 7A:
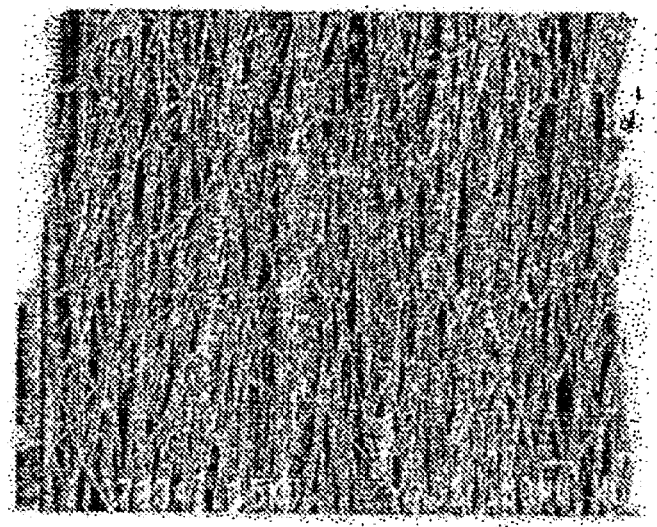
Figure 7B:
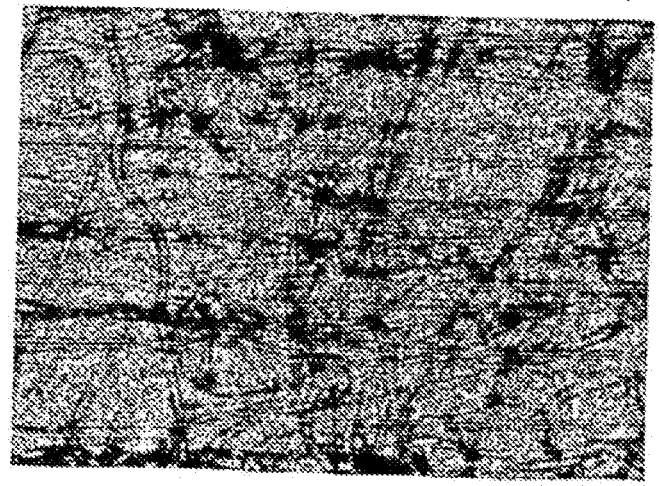
Figure 8A:
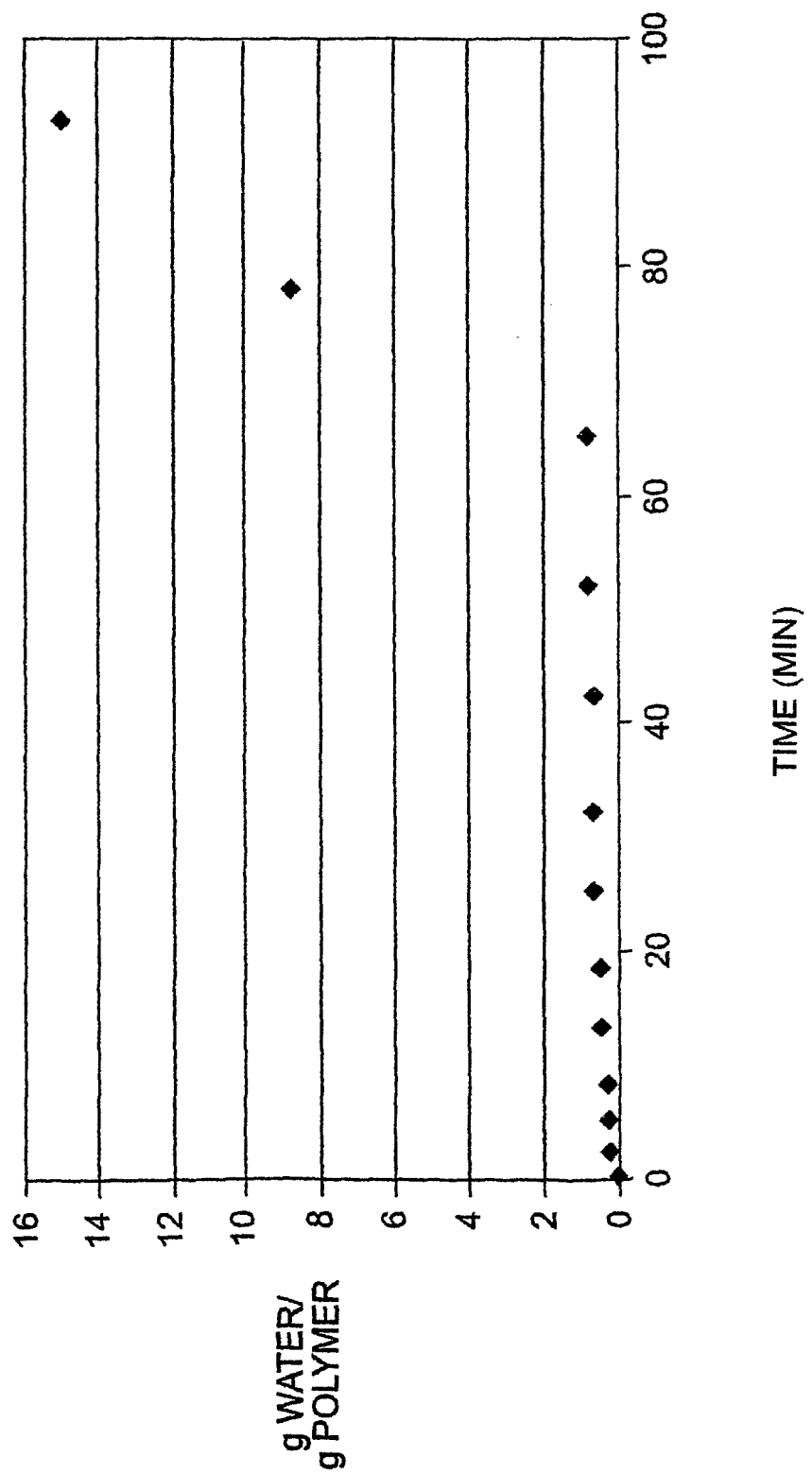
Figure 8B:
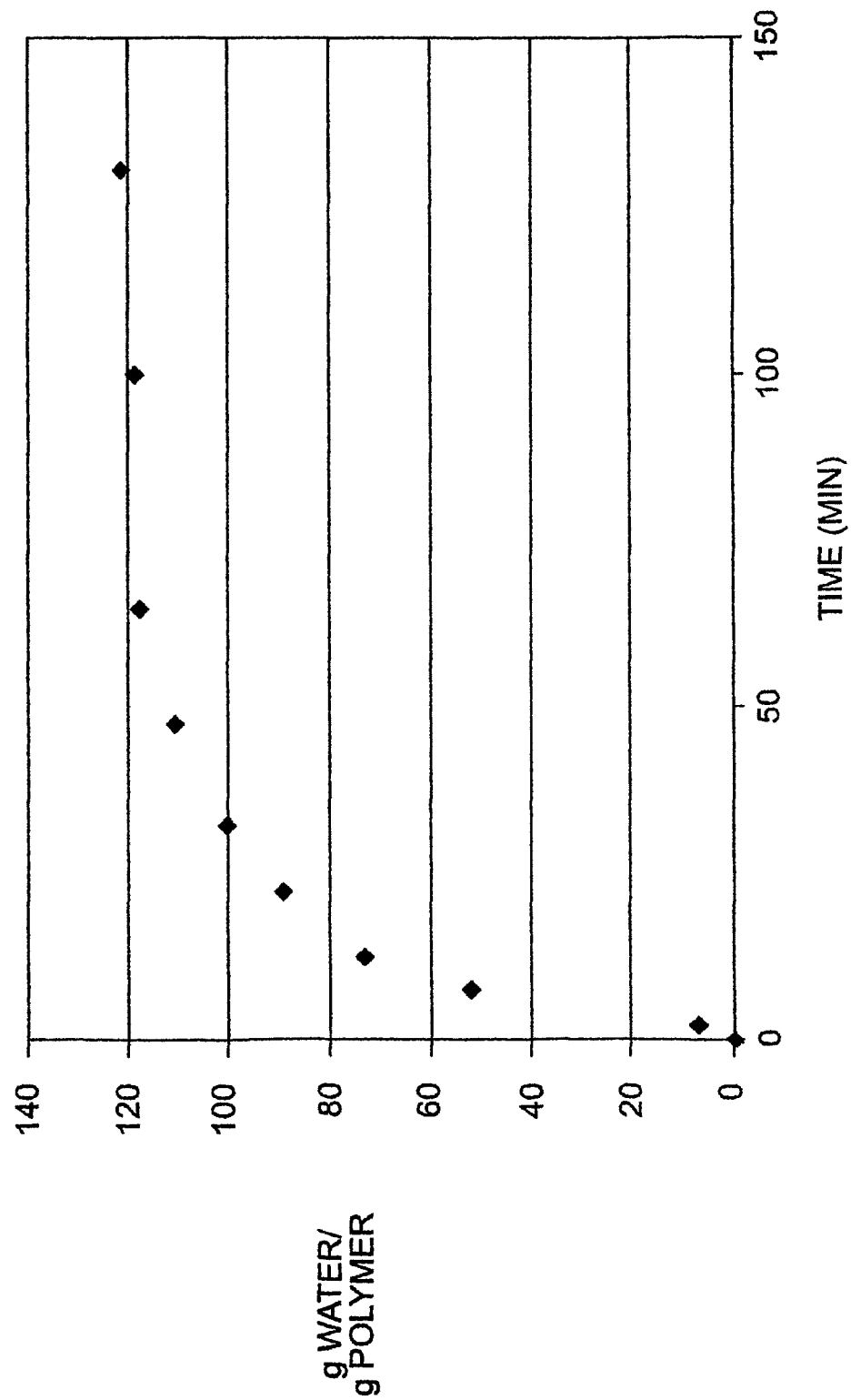

FIG. 7A is a scanning electron microphotograph of an ethylene vinyl acetate (EVA) electrospun mat; FIG. 7B is a scanning electron microphotograph of EVA FIGS. 8A-8B are a graph of swelling properties of swellable materials according to the invention electrospun ethylene-vinyl acetate (EVA) copolymer bags, with time (minutes) plotted against grams water/grams polymer, for poly(acrylamide)co-acrylic acid copolymer (FIG. 8A) and poly(acrylamide)co-acrylic acid copolymer potassium salt (FIG. 8B), respectively.

Figure 9A:
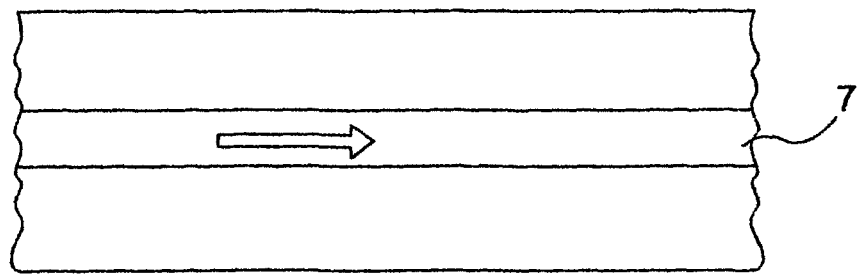
Figure 9B:
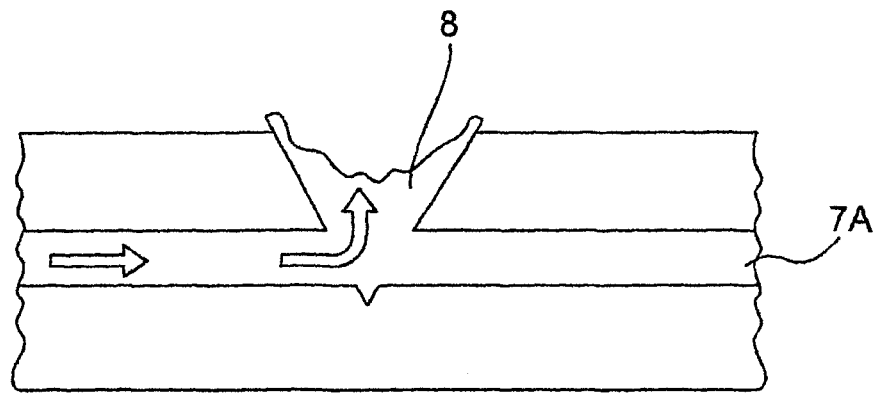
Figure 9C:
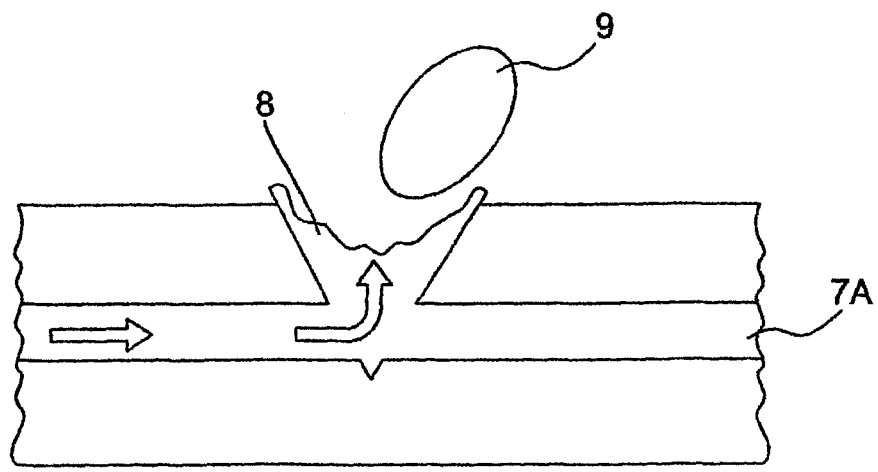
Figure 9D:
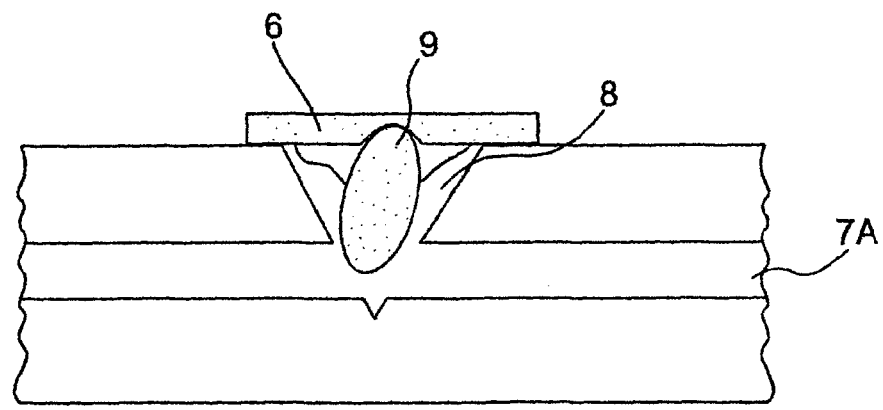

FIGS. 9A-9F are representational cross-sections of an initially healthy blood vessel (FIG. 9A) that is disrupted (FIG. 9B), with the invention used in treating the disrupted blood vessel FIGS. 9C-9D).

Figure 10B:
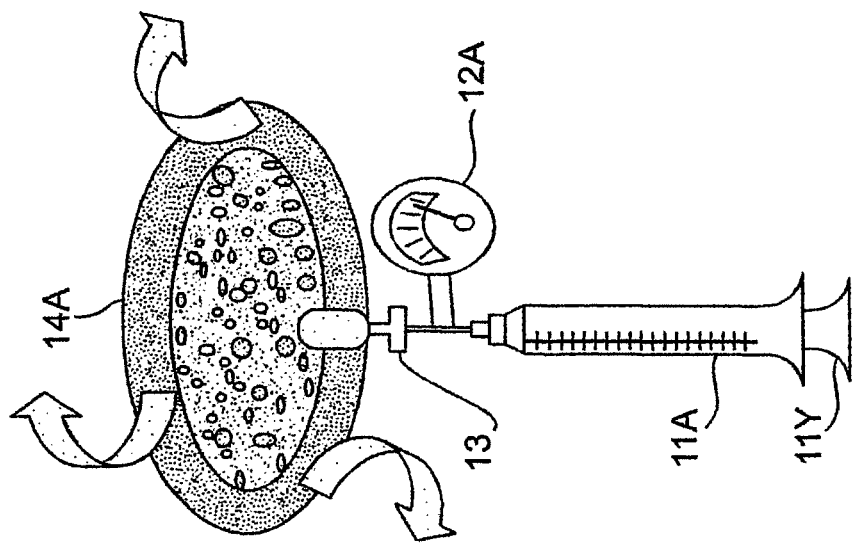
Figure 10A:
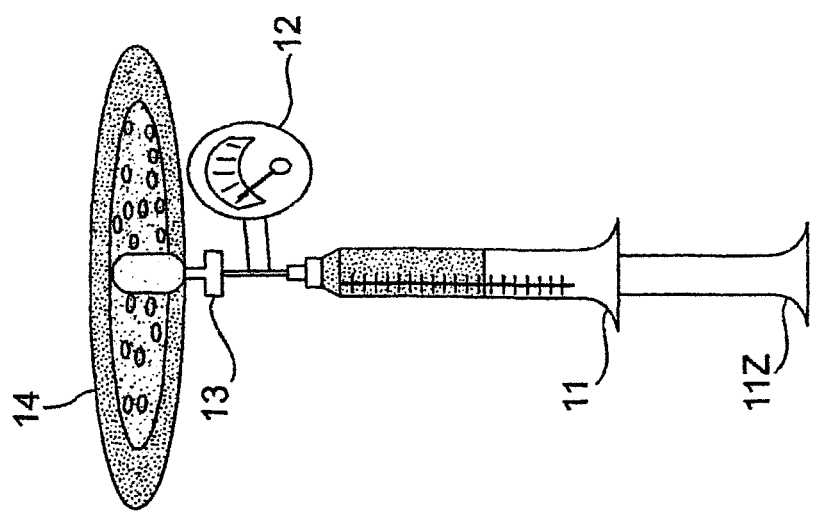

FIGS. 10A-10B diagram filling according to the invention.

FIG. 11 is a representative view of an exemplary layered-system device according to the invention.

Figure 12:
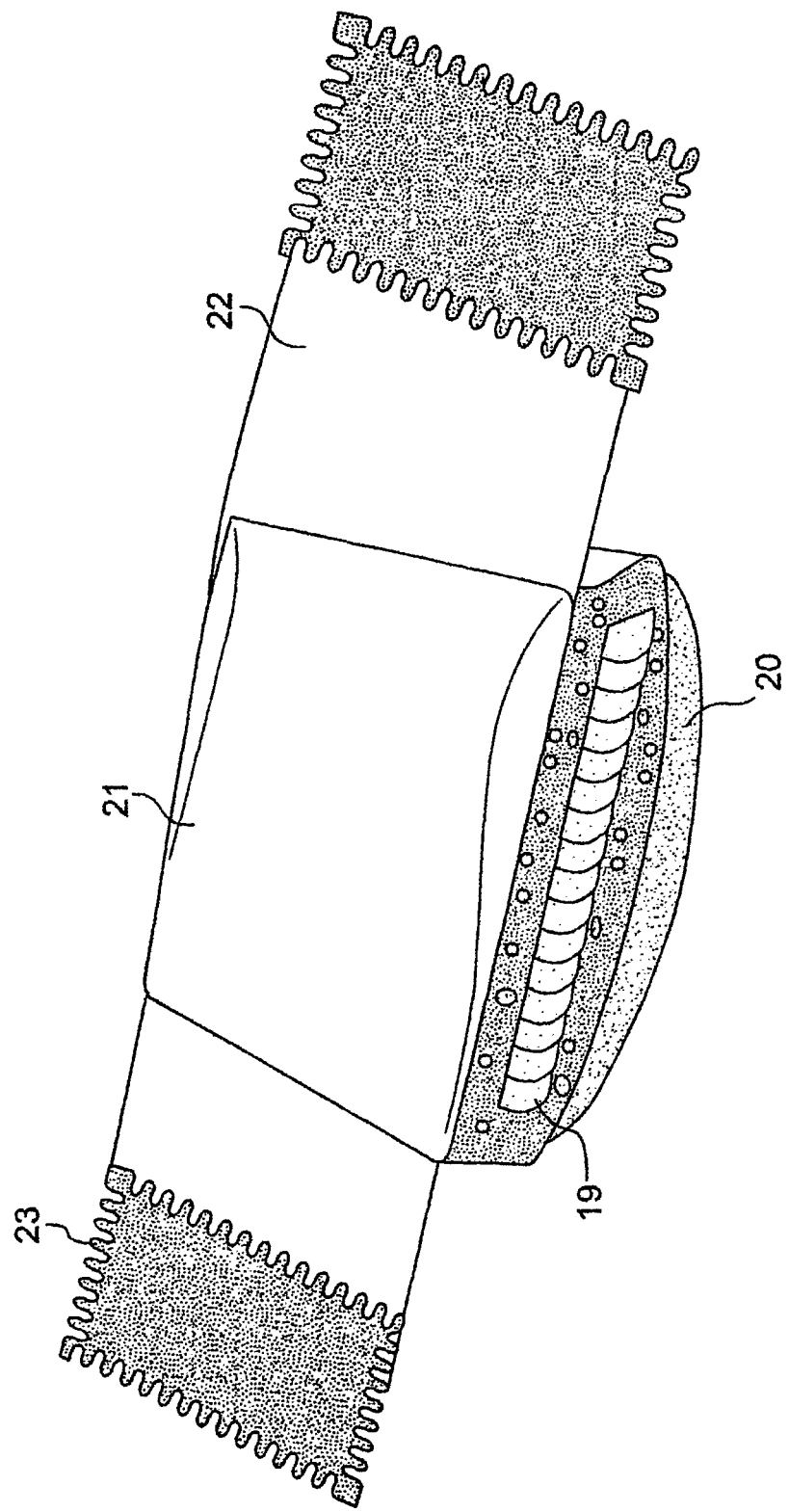

FIG. 12 is an exemplary system according to the invention for use with external hemorrhage.

DETAILED DESCRIPTION OF PREFERRED EMBODIMENTS OF THE INVENTION

With the invention, a liquid leak (such as a bleeding wound, etc.) may be stopped or at least reduced by applying direct pressure inside the leak. The direct pressure to be applied may be generated by a swellable material, by pneumatic filling of a bladder, singly or in combinations thereof etc.

Where a swellable material is used, the swellable material is selected based on the leaking liquid to which it will be exposed, such as blood in a patient, water in a plumbing system, etc. Most preferably, the swellable material absorbs at least 10 times its weight of the leaking liquid, such as, in the case of bleeding, about 10 times its weight of water.

In a particularly preferred embodiment, the invention provides an exemplary method of treating a bleeding wound, comprising applying direct pressure directly in the bleeding wound, most preferably applying direct pressure in the range of about 50 to 90 mm Hg directly in a high-pressure bleeding wound (such as a wound bleeding at about 60 to 90 mm Hg pressure). The wounds treatable by the invention include high-pressure bleeding wounds, compressible wounds, non-compressible wounds, external wounds, etc. The invention advantageously may be used for treating wounds bleeding in a range of about 60 to 140 mm Hg, or higher, and also may be applied for treating low-pressure bleeding.

In the case of high-pressure bleeding wounds, a preferred example of applying direct pressure directly in the bleeding wound is to insert a hemostatic (i.e., hemocompatible direct-pressure-producing) substance or article into the wound and to enclose the wound with the hemostatic substance or article therein. By establishing around the wound a confined space, such as the wound covered with an elastic dressing, swelling of a swellable material enclosed therein may be used to produce a back pressure that advantageously stops or at least slows bleeding. By provision of such a back pressure within the wound, clot formation may be supported and enhanced, and high pressure (arterial) bleeding may be stopped or at least slowed, advantageously without compromising collateral blood flow (as occurs with a constrictive treatment such as a tourniquet).

The application of direct pressure preferably is pressure generated by swelling of at least one swellable material. The amount of pressure applied is in an amount for stopping or at least minimizing bleeding from the wound, preferably such as about 50 to 90 mm Hg pressure (most preferably, about 80 mm Hg pressure) generated from a swelling substance or article in four minutes or less (most preferably about three minutes or less).

As preferred examples of swellable materials for use in the invention may be mentioned polymers, such as polymers that are hydrogel-forming, micro-fibrous and/or water-absorbing, poly(acrylic acid), poly(ethylene oxide), poly(acrylamide), hydroxypropyl cellulose, other polymers or substances used in diapers and/or incontinence pads, etc., and their salts (such as ammonium, sodium, etc.) and derivatives thereof. Most preferred examples of swellable materials are swellable hemostatic substances including the following: poly(acrylic acid); polyacrylamide polyacrylamide (crosslinked); poly(acrylic-co-acrylamide) crosslinked (such as N, N-methylene bis-acrylamide crosslinked); crosslinked and modified polyacrylamide; polyhydroxyethyl methacrylate) PHEMA; hydrogels based on poly(vinyl alcohol) (PVA); alginate based hydrogels; HEM-coacrylic acid-co-sodium acylate copolymeric hydrogels; isopropylacrylamide-co-acrylic acid-co-sodium acrylate hydrogels; and gelatin gels. Some polymer structures are shown in Table 2, below.

TABLE 2

Examples of absorbent polymers

| Polymer | Structure |
|---|---|
| Poly (acrylic acid) (linear) | $-(CH_2-CH)-$<br>$\phantom{-(CH_2-}\|$<br>$\phantom{-(CH_2-}COOH$ |
| Polyacrylamide Polyacrylamide (Crosslinked) (linear) | $-(CH_2-CH)-$<br>$\phantom{-(CH_2-}\|$<br>$\phantom{-(CH_2-}CONH_2$ |
| Poly(acrylic-co-acrylamide) crosslinked (N,N-methylene bis-acrylamide crosslinked) (linear copolymer structure) | $-(CH_2-CH)_n-(CH_2-CH)_m-$<br>$\phantom{-(CH_2-}\| \phantom{-(CH_2-CH)_n-(CH_2-}\|$<br>$\phantom{-(CH_2-}COOH \phantom{-(CH_2-CH)_n-}CONH_2$ |
| Crosslinked and modified Polyacrylamide | $-(CH_2-CH)-$<br>$\phantom{-(CH_2-}\|$<br>$\phantom{-(CH_2-}CONH-X$<br>X = various groups |
| Poly(Hydroxyethyl methacrylate) PHEMA (linear) | $\phantom{xx}CH_3$<br>$\phantom{xx}\|$<br>$-(CH_2-C)_n-$<br>$\phantom{xx}\|$<br>$\phantom{xx}COOCH_2CH_2OH$ |
| Hydrogels based on Poly(vinyl alcohol) PVA (linear) | $-(CH_2-CH)_n-$<br>$\phantom{-(CH_2-}\|$<br>$\phantom{-(CH_2-}OH$ |

"n" = an integer
"m" = an integer which may be the same or different from "n"

As to the polymer size, preferable to use are polymer fibers of diameter about 10 microns or less, most preferably 1 micron or less. That small-diameter polymer fibers are particularly preferred may be seen by considering that, for a gel fiber, the contraction rate t is equal to a contraction rate constant c times the square of the diameter; this relationship may be used to evaluate particular polymer fibers (such as fibers of particular diameters) for whether they have rapid swelling kinetics. For example, for polyacrylamide, c is approximately $2 \times 10^9$ s/m$^2$ and therefore polyacrylamide gels with a diameter of 1 cm take about 2.5 days to swell, while micron diameter polyacrylamide fibers take milliseconds. See E S Matsuo, T Tanka, "Kinetics of discontinuous volume-phase transition of gels," J Chem Phys, 89:1988 (1988).

For formulating polymers useable in the invention, preferably electric field-mediated polymer processing is used, most preferably with electrospraying and/or electrospinning. J Stetzel, G L Bowlin, K Mansfield, G E Wnek, D G Simpson, "Electrospraying and electrospinning of polymers for biomedical applications, poly(lactaic-co-glycolic acid) and poly (ethylene-co-vinylacetate), Proc. SAMPE Conf., Boston, November 2000; D H Reneker, I Chun, "Nanometer diameter fibers of polymer produced by electrospinning," Nanotechnology, 7:216-223 (1996). Electrospinning may be used to afford small diameter (i.e., 10 microns or less) hydrogel-forming polymer fibers having rapid swelling kinetics.

Starting materials suitable for electrospinning or electrospraying include elastomeric materials such as thermoplastic elastomers, such as segmented polyurethanes, ethylene-vinylene acetate (EVA) copolymer, etc. Biocompatible starting materials (such as EVA copolymer) are particularly preferred, and biocompatible starting materials that serve as a host for the delivery of a wide variety of small and large therapeutic molecules (such as EVA copolymer) are most preferred. J Folkman, R Langer, "Polymers for the Sustained Release of Proteins and Other Macromolecules," Nature, 263:797 (1976). Although theoretically non-biocompatible materials could be used if enclosed in an expandable impermeable membrane (such as a syringe port), such a course is not preferred and to be avoided when the starting materials are to be used to formulate a system for wound treatment or other use on or in a patient.

Figure 1A:
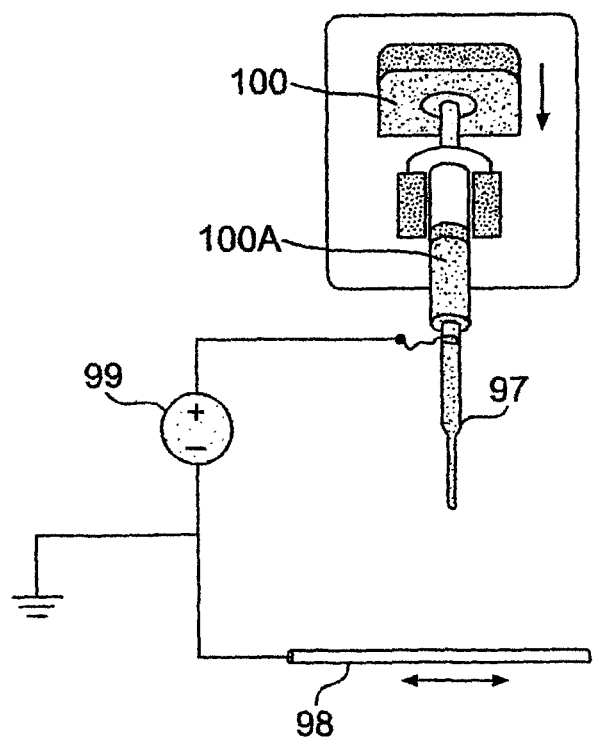
FIG. 1A is a schematic of an apparatus for electrospraying or electrospinning production.

As shown in FIG. 1A, an apparatus for an electrospraying or electrospinning system comprises a syringe pump 100 for pumping a starting material solution or melt 100A to be sprayed or spun, a high voltage system 99 (such as a 15 kV system), a collector (ground) electrode 98, and a source electrode 97. The starting material solution or melt 100A is preferably confined in any material formed into a nozzle with various tip bore diameters (such as a disposable pipette tip), with a very thin source electrode 97 immersed in it. The collector 98 can be a flat plate, wire mesh, rotating metal drum or plate on which the polymer is wound, etc. The solution 100A to be spun or sprayed can be doped with various substances, such as, in the case of electrospun fibers, doping with various substances that can be released from the electrospun fibers. The electrospinning process preferably is continued until a mat accumulates (such as an EVA mat) of approximate dimensions as desired, such as on the order of mm by mm, or cm by cm by length and width, and micrometers to millimeters for thickness.

Additionally, swellable materials may be obtained commercially, such as alginate based hydrogels; HEMA-co-Acylic acid-o-Sodium acylate copolymeric hydrogels; poly (vinyl alcohol)/poly(acylic acid) hydrogels; isopropyylacrylamide-co-acrylic acid-co-sodium acrylate hydrogels; gelatin gels; etc.

When a polymer is used as the swellable material, the polymer may be uncrosslinked or crosslinked, preferably crosslinked. Crosslinking can be accomplished during polymerization with the use of polyfunctional monomers such as bisacrylamide, or by treatment of the polymer with ionizing radiation (e.g., □-radiation). Where electrospinning is carried out from solution or the melt using uncrosslinked polymers, preferably the polymer is treated with ionizing radiation.

The swellable material may be provided for use with a leaking material in a variety of forms, such as a mat of a swelling material, a swelling material contained within a shell or membrane, a swelling material dispensed from a tube or aerosol, etc. The form used may be selected based on the characteristics of the leak to be treated, the likely treatment setting, etc.

In the case of wound treatment, especially high-pressure wound treatment, the swellable material preferably is contained within a biocompatible, hemocompatible shell or membrane that permits the leaking liquid to pass through the shell or membrane to reach the swellable material. The shell or membrane is selected with regard to the leaking material (such as blood), the swellable material, and any other treating material (such as clotting promoters, antibiotics, analgesics, etc.) disposed within the shell or membrane. For selecting a shell or membrane, preferably, the shell or membrane is porous, elastic, provides stiffness as the hydrogel inside swells, and/or allows easy ingress of the particular leaking material (such as blood), and most preferably meets all of these characteristics. Elastomeric polymers and hydrophilic, expansile polymers are particularly preferred as shells or membranes as they typically increase in stiffness when stretched due to chain orientation. Such stiffening of the shell upon swelling of the interior hemostatic substance or article is desirable for generating back pressure. Preferably the to-be-used membrane is formed as a relatively flat bag, with relatively little unoccupied space around the swellable material. Loose-fitting placement of the swellable material within the membrane is preferred, corresponding to the expansion geometry. Namely, as the membrane limits the material expansion, a too-tight between the swellable material and the membrane is not desired because expansion of the membrane would be impeded. Namely, if membrane expansion is limited, correspondingly the amount of pressure that the membrane is able to put on its surroundings (such as a bleeding wound) is limited. The membrane preferably is non-leaking with regard to the swellable material, and, where a polymer is used as the swellable material, polymer leakage may be minimized by crosslinking the outermost portions of the polymer matrix to the membrane.

When a membrane is used for enclosing the swellable material, preferably the membrane is perforated. Pore sizes are such as to limit the leakage of polymer; the pores can increase with swelling because the size of the polymer inside increases as it binds the water, permitting more blood/water to enter and bringing about equilibrium. The membrane is not required to be completely uniform in its characteristics, and may be customized. For example, where the membrane is perforated, most preferably the perforations are relatively large and numerous on the part of the membrane that is to contact the bleeding (or other leaking material), so that exiting blood and other liquid may enter the membrane and activate the swellable material so that the swellable material swells and exerts a backpressure. It will be appreciated that if the membrane where it contacts the wound is resistant to the exiting blood and liquid and does not permit their entry, they will find an alternate path, i.e., traveling around the resistant membrane and exiting the wound; thus, a too-resistant membrane on the wound side is to be avoided as the swellable material would not be swelled.

Customizing the membrane on the non-wound side (i.e., the dressing side or medic side) may include features to retain the swelled material, blood, liquid, etc., such as non-perforation, reinforcement of the membrane, coating, etc. It will be appreciated that on the non-wound side, it is not desired that blood, body fluids, or other materials escape. Where a customized membrane with a wound-side and non-wound differential is used, the person to be applying the membrane-enclosed swellable material will require training and/or specific markings on the membrane are included. In determining whether to customize a membrane or to provide a unitary membrane, there may be considered the training of the person who will administer the membrane-enclosed swellable material, whether the membrane can be marked to direct the person administering the swellable material which side to place into the wound, etc.

To the hemostatic substance or article and/or to the shell there may be added further substances, such as a clot-promoting substance (such as thrombin, preferably lyophilized thrombin). Including a clot-promoting substance in the shell advantageously promotes blood clotting around the periphery of the shell. Preferably, a concentration of the clot-promoting substance is one that speeds clotting without clogging the swellable material with clot.

It will be appreciated that, until ready for use, the swellable material must be kept away from materials which may cause it to swell. For example, in the case of a swellable material intended for use with blood and aqueous materials, the swellable material must be kept dry.

Figure 4A:
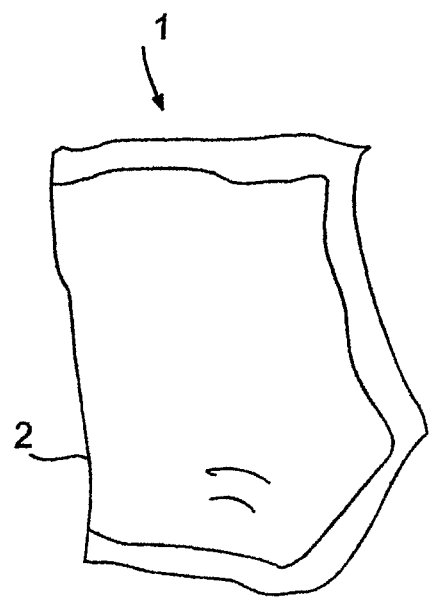
FIGS. 4A-4B are perspective views of a medical device according to the invention, with FIG. 4A showing a wound treatment device before use and FIG. 4B showing a wound treatment device expanded after exposure to blood, water or another liquid.
Figure 4B:
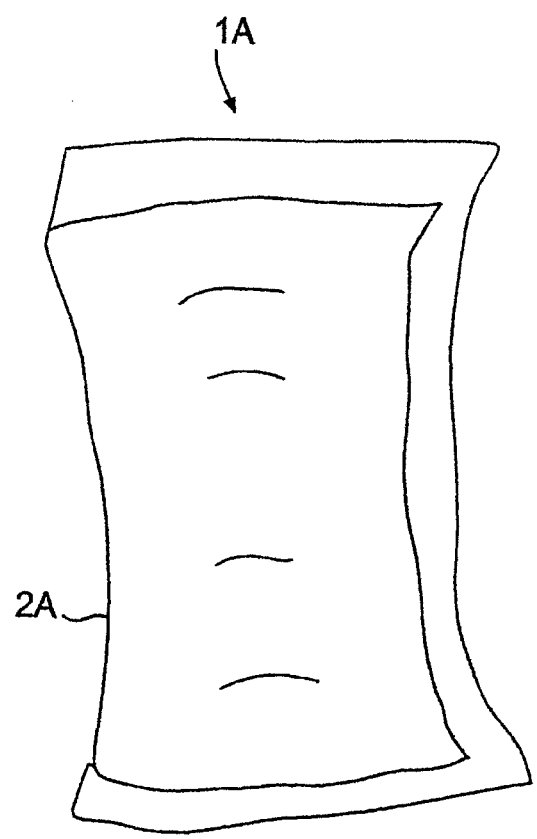
Figure 5A:
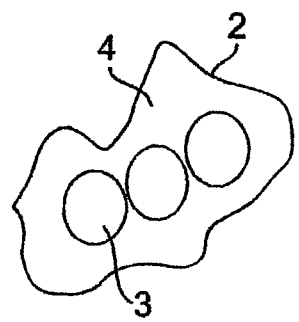
FIGS. 5A-5B are representational views of a molecular scale depiction of behavior of a device according to the invention.
Figure 5B:
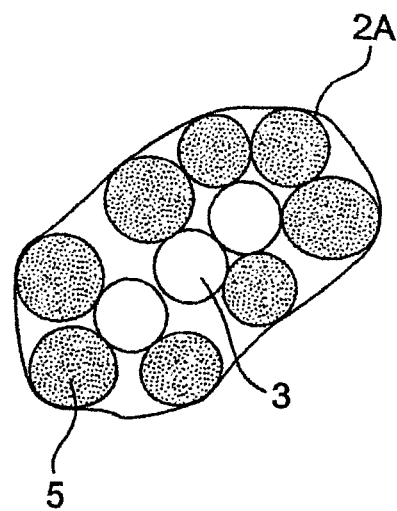

The invention also provides certain devices (such as medical devices), especially those comprising a swellable material (as mentioned above) within a shell (as mentioned above). Most preferable devices are those such as that of FIGS. 4A-4B, FIGS. 5A-5B and FIGS. 6A-6C. As shown in FIG. 4A, before exposure, a device 1 of which the exterior is a membrane 2 is relatively small in size. FIGS. 5A and 6A are respective molecular-scale versions corresponding to FIG. 4A, with some molecules 3 constituting the swellable material shown. (Only a few swellable material molecules 3 are shown for simplicity; it will be appreciated that generally a device comprises a large population of molecules 3). Before the device has been exposed to a liquid, the membrane 2 is loose and there is a void 4 inside the membrane 2 (FIG. 5A).

As shown in FIGS. 6A-6C, a device comprising a swellable material 3 within a membrane 2 is contacted with a leaking material 5 (such as blood) and the leak (such as a wound) is enclosed with an enclosure material 6 (such as a dressing).

Membrane 2 on the wound side 2Y permits leaking molecules (such as blood molecules, water, etc.) 5 to pass into the interior of the device, and that as such blood molecules, water and other leaking molecules 5 come in contact with swellable material molecules 3, the blood and other water-containing molecules 5 bond to the molecules 3 and remain inside the membrane, causing the membrane to expand. At a certain point expanded membrane 2A has reached its maximum expansion for the pressure being applied by the leaking molecules 5. Leaking molecules 5 inside the membrane 2A cannot readily exit the membrane 2A on the wound side 2Y because more leaking molecules 5 are entering at the wound side 2Y of the membrane 2A. While some leaking molecules 5 may escape through expanded membrane 2A at the dressing side 2Z of the membrane 2A, the relatively greater number of leaking molecules 5 that have been retained within in the device and within the wound should be appreciated. Additionally, the membrane 2 on the dressing side 2Z during production may have been reinforced or treated to be relatively less porous or less perforated than on the wound side 2Y.

As the device is used in a bleeding wound, the swellable material 3, the leaking molecules 5 contained within the membrane 2A, the membrane 2A (including the membrane 2A on the wound side 2Y and on the dressing side 2Z) together and respectively act as a barrier to leaking molecules 5 that are newly approaching the membrane 2A on the wound side 2Y, so that where leaking molecules 5 earlier had encountered no or little force blocking their exit, they encounter some back-pressure (FIG. 6B) as the device operates and then as the device is maximally activated, they encounter pressure equalization (FIG. 6C).

During exposure to a liquid, device 1 accepts additional molecules and membrane 2 expands, forming expanded device 1A (see FIG. 4B) of which the exterior is expanded membrane 2. Such expansion is possible because a swellable material within the device controllably swells when exposed to aqueous solutions (such as found in a bleeding wound), with the desired result of the expansion being to generate a back pressure. When a medical device containing a swellable material is introduced into a bleeding wound, and the wound and device enclosed together, bleeding can be stopped or at least reduced by the back pressure generated by the device.

An exemplary device 1 according to the inventive is a clotting-promoter containing device, such as a thrombin-containing device. An example of using a clotting-promoter containing device may be appreciated with regard to FIGS. 9A-9E. In FIG. 9A is shown a healthy blood vessel 7 (such as a vessel having a typical pressure of T=90 mmHg). The healthy blood vessel 7 suffers injury and becomes disrupted blood vessel 7A (FIG. 9B) having a wound 8. In FIG. 9C is shown moving a clotting-promoter containing device 9 (such as a thrombin-containing device) towards the bleeding wound 8. In FIGS. 9A, 9B and 9C, arrows show the direction in which blood travels. As shown in FIG. 9D, the device 9 is inserted directly into the bleeding wound 8, and covered with a dressing 6. Once the device 9 is provided into the bleeding wound 8, blood begins to enter the device 9 and to contact the dressing 6.

Figure 9E:
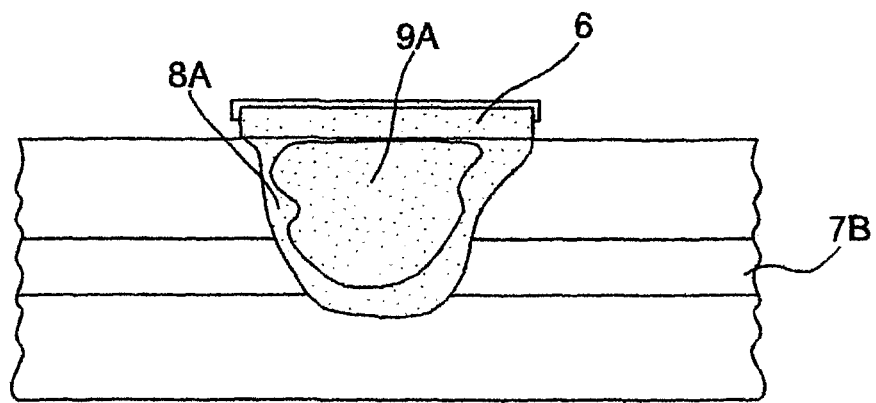

After the device 9 has been in the wound 8 held by the dressing 6 for a time (such as about three minutes), the device will have expanded and will have released clotting-promoters, with the wound 8A containing clotting promoters, as shown in FIG. 9E. Expanded device 9A as a result of its expansion exerts pressure on its environment, namely on the patient's blood. In addition to the pressure exertion effects provided by expanded device 9A, the bleeding wound 8A also experiences clotting promotion from the clotting promoters released from the device 9, 9A.

Figure 9F:
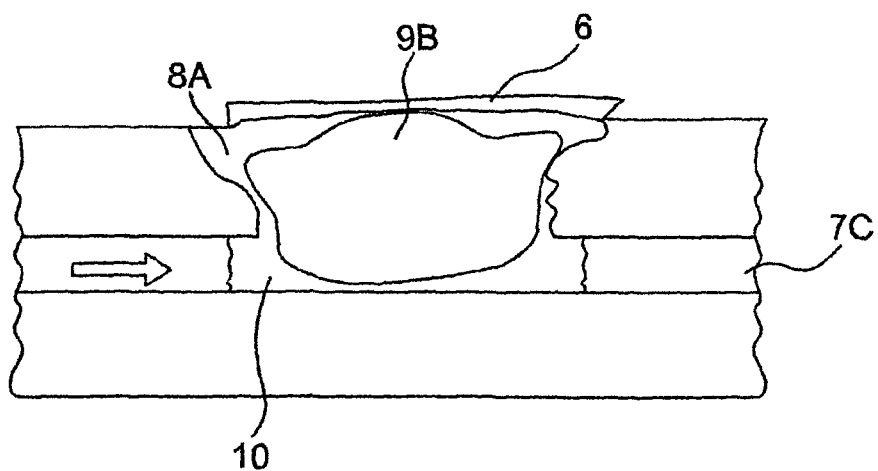

As the expanded device 9A continues to expand (see FIG. 9F), such as at about four minutes after device insertion, the more-expanded device 9B will take up more space in the wound. As time progresses (see FIG. 9F), such as about four minutes pass since insertion of the device 9 into the bleeding wound, further-expanded device 9B exerts an equalized pressure on its surroundings in the wound 8A, and a pressure equilibrium is reached. As the clotting promoters take further effect, clotted regions 10 are formed. The equilibrium situation of FIG. 9F is maintained. Advantageously, the expanding device 9, 9A, 9B reduces and stops blood loss. In this particularly preferred inventive embodiment shown in FIGS. 9C-9F, direct pressure application inside the wound is combined with clotting promotion to stop blood loss from a penetrating wound in as little as 3 or 4 minutes, or even less.

FIGS. 9C-9F show a device 9, 9A, 9B being used to treat a bleeding wound, with the fresh device 9 slightly smaller than the wound 8 into which it is being placed. When selecting a device size for inserting into a bleeding wound, it is desired that the expanded device 9B be of a volume at least equal, preferably greater, than the wound. Thus, when confronted with a wound 8 for treatment, it is desirable to use a device 9 that will expand into an expanded device 9B of greater volume than the wound to be treated. Devices 9 of different starting size may be provided. Also, depending on the swellable material used, expanded devices 9B of different volumes may be provided.

Further, combinations of two or more devices (such as device 9) may be used for treating a bleeding wound, such as treating a relatively large penetrating wound with two or more devices (which may be the same or different). In determining how many devices 9 to use, or what expanded device 9B may be desirable for a particular bleeding wound to be treated, it is preferred to insert into the wound a higher direct-pressure application capability than may be needed (such as to use more devices 9 or a device 9 having the potential of a larger-volume expanded device 9B than may be needed to stop bleeding), than to insert into the wound insufficient direct-pressure application capability to stop the bleeding.

In the case where an initial application of direct pressure in the wound (such as insertion into the wound of a first device 9 that expands into expanded device 9B) only reduces bleeding but is insufficient to stop bleeding, further direct pressure in the wound (such as insertion into the wound of a follow-up device) may be applied.

When bleeding stops after insertion of a device 9 into a bleeding wound, expanded device 9B may be permitted to remain in the wound or may be removed. Whether to remove the expanded device 9B or not may be based on factors such as need for access to an internal area for surgery, etc. Preferably the device 9B is left in the patient unless a reason appears for removing the device 9B.

In using the invention, formulations are desired that promote clotting at a rate of preferably about less than one minute, with relatively faster clotting being preferred. Clotting is desired to proceed apace with the swelling, with clotting to be complete as expansion is complete. Promoting more rapid clotting raises the possible complication of clotting before the device swells sufficiently to develop adequate back pressure. For a device comprising a membrane-encased swellable material, approximate clotting rate can be provided by the amount of hemostatic agent and/or amount of clotting promoter used, and/or by the size and amount of pores in the membrane.

For the direct pressure useable in the invention, another technique for generating direct pressure comprises filing (such as pneumatic filing, etc.) of a bladder, most preferably, a bladder comprising a membrane enclosing a swellable material wherein the swellable material swells on contact with the leaking material (such as blood in a bleeding wound). An exemplary filling process according to the invention is shown in FIGS. 10A-10B, As shown in FIG. 10A, a device 14 (which may be device 9) is provided with a syringe port 13 for receiving a syringe 11 (such as a syringe containing a volume of clotting promoter (such as thrombin) or other biocompatible material; a syringe containing air; a syringe containing water or another liquid, etc.). An initial-setting pressure monitor 12 is provided. Upon depressing the syringe plunger 11Z, the contents of the syringe 11 are transferred through the syringe port 13 and the device 13 is inflated. As shown in FIG. 10B, depressed syringe plunger 11Y corresponds to activated pressure monitor 12A. The inflated device 14A by virtue of its greater volume provides direct pressure on its surroundings (shown by arrows). The device 14A may be inflated entirely due to pneumatic filling, or may be inflated by pneumatic filling combined with one or more other inflating methods (such as swelling of a swellable material).

A filler according to the invention may be separable from, or attached to, the device into which it is inserted. The device into which the filler is inserted may be a bladder with or without a swellable material contained therein, such as a bladder comprising a membrane as mentioned herein. As preferred examples of a bladder may be mentioned an elastic non-permeable bladder, an impermeable bladder, a permeable membrane, singly or in combinations thereof, etc.

A device according to the invention optionally may comprise a layered system, such as a layered system of membrane(s) (such as a permeable membrane), bladder(s) (such as an impermeable bladder), membrane contents, and/or bladder contents. An exemplary layered system 15 is shown in FIG. 11, comprising an impermeable expandable bladder 16 inside a permeable membrane 17. The expandable bladder 16 may be expanded by adding water, air, etc., such as addition through syringe port 13 using syringe 11. Between the membrane 17 and the bladder 16 no contents are required but most preferably are included contents 18 comprising one or more of a swellable material (such as an absorbent polymer), a clotting promoter (such as thrombin), antibiotics, analgesics, anesthetics, singly or in combination, etc. As contents 18, a swelling material preferably included, most preferably a swelling material including an absorbent polymer.

A layered system 15 preferably may be used by, once the layered system 15 is placed in a bleeding wound, inflating or expanding bladder 16. The expansion of bladder 16 applies force to the contents 18 in the direction of moving the contents 18 towards the membrane 17. Where a swellable material is included in contents 18, the swellable material preferably is treated (such as by crosslinking) to minimize passage of the swellable material out of the membrane 18. Where a clotting promoter (such as thrombin), antibiotics, analgesics, and/or anesthetics are included in contents 18, such materials are provided in a form to maximize their passage through the membrane 18 and to the exterior of the system 15, and their expulsion from the system 15 is aided by the expansion of the bladder 16 and/or swelling of any swellable material in contents 18.

The inventive methods and devices are particularly usable by a combat medic in treating bleeding wounds such as combat wounds. As to early treatment of combat wounds, it will be appreciated that the combat medic is a skilled individual, and may readily use the invention. Inventive methods and devices also may be used by less skilled or relatively unskilled individuals in treating bleeding wounds.

Advantageously, the invention provides the treatment paradigm of saving the patient without compromising limb salvage. An acute treatment is provided for both civilian and military medical treatment of penetrating wounds, in human and veterinary medicine. The wounds that may be treated include wounds suffered by human patients and by animals; battlefield injuries and civilian injuries; etc. The invention advantageously stops bleeding without producing pressure injury or ischemic damage. By retaining the patient's blood, the amount of transfused blood is reduced, and the risks associated with transfusion are correspondingly reduced.

While particular mention has been made herein of the invention's applicability for treating penetrating injuries, external wounds are treatable using the present invention, such as by applying (e.g., self-applying, medic-applying, etc.) a wound care dressing comprising a swellable material to the external wound. Where an external wound cannot receive immediate definitive treatment, application of a wound care dressing according to the invention provides a preferred holding treatment. A wound dressing according to the invention promotes hemostasis, prevents infection, and/or relieves pain, delivering one or more features in a relatively quick time frame. The external wound dressings may be self-administrable. A exemplary system according to the invention for treating an external wound is shown in FIG. 12, with the system comprising a swellable material 19 (such as an absorbent polymer) disposed behind a porous membrane 20 (such as a telfa pad) to be placed in contact with the to-be-treated external wound. To the swellable material 19 optionally may be added one or more of a clotting promoter (such as thrombin), an antibiotic, an analgesic, an anesthetic, etc. An impermeable material 21 (such as an impermeable plastic) is provided for avoiding contact of the swellable material 19 and/or the membrane 20 with the air, etc. A fastener system is provided attached to the impermeable material 21, with a fastener system comprising an elastic fastener 22 and a Velcro material 23 being preferred. A fastener system (such as a Velcro-free adhesive fastener system, etc.) may be provided depending on the size and/or location of the wound-to-be treated.

While much discussion has been provided of the invention's use in connection with wounds, especially penetrating wounds, and limbs, the invention may be extended to other forms of bleeding (such as intra-abdominal and intra-pleural), including bleeding that otherwise would be difficult to treat (especially in the acute setting). The device is placed in the wound, expanded, and held in place (at least initially) by mechanical pressure.

The invention further provides a drug delivery system (such as a time released drug delivery system), usable in the presence of a wound (such as by insertion into the wound) or absence of a wound (such as by ingestion, surgical implantation, etc.). Such a drug delivery system comprises a swelling material and at least one drug (such as a hemostatic agent, antibiotic, analgesic, etc.). A swellable material (such as a polymer system) may be used as a drug delivery system such as to simultaneously enhance hemostasis, prevent infection and/or provide pain relief to acute non-penetrating injuries. E.g., such a drug delivery may be provided as a self-administered dressing (such as an acute dressing). Advantageously, such a self-administered dressing may prolong the "golden period" between injury and treatment.

While much has been said above about bleeding and medical applications of the invention, it will be appreciated that the invention provides leakage control systems extending beyond the medical and bleeding areas, such as to pressure equalization techniques for a quick temporary plug for any type of liquid high pressure leak (such as a plumbing leak, a boating leak, a container or tanker leak, etc.). Any system where even temporary drops in pressure due to leakage is a significant problem may benefit from the inventive pressure equalization methods. Leaks may be treated by inserting a swellable material into the leak, preferably while maintaining the swellable material in the leak. Where the leak does not involve treating a patient, less biocompatibility may be acceptable than for treatment of wounds, wound dressings, etc. The swellable material is selected based on the leaking liquid to which the swellable material will be exposed. Where the leaking liquid is water or water-based, the water absorbent swellable materials mentioned above for wound treatment may be used.

Figure 3:
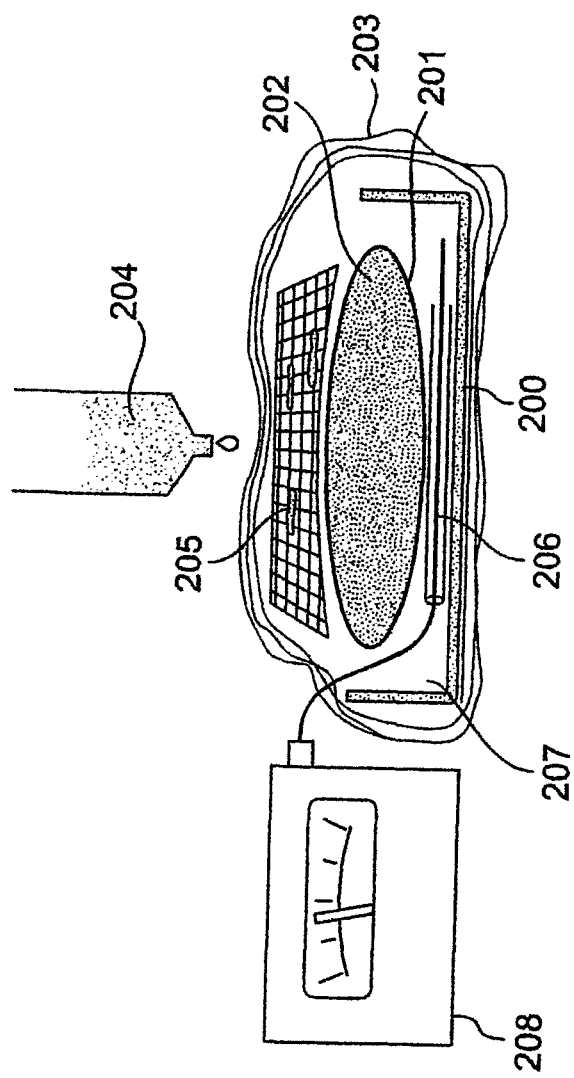
FIG. 3 is a screening apparatus for substances for pressure development during swelling in a confined space.

The invention also provides a screening apparatus for evaluating the efficacy of a particularly formulation of a swellable material (such as a polymer) when in contact with a particular leaking material (such as a watery liquid), with an exemplary screening apparatus that may be used to screen substances for pressure development during swelling in a confined space shown in FIG. 3. Substances (such as polymers of varying diameters) may be tested for compaction, flexibility and ability to rapidly swell in the presence of liquid. The ability of a substance to produce pressure in a confined space may be evaluated using a screening apparatus, such as the exemplary apparatus shown in FIG. 3. With reference to FIG. 3, a receptable 200 (such as a petri dish) is provided for receiving a to-be-tested substance 202, such as a to-be-tested substance is contained in a highly perforated flexible membrane 201 (such as thin latex). The to-be-tested substance is placed in the receptable 200 and secured there by a wrap 203 (such as by a cling gauze wrap), optionally including other materials such as a gauze pad 205. Liquid to be poured onto the upper surface of the to-be-tested substance is disposed in a bathing solution container 204. A pressure probe 206 is placed between the membrane 201 and the wall of the receptable 200. As liquid is poured on the upper surface of the to-be-tested substance, the pressure within the confined space 207 is monitored by the pressure probe 206 hooked to pressure monitor 208. A baseline criterion of a certain amount of generated pressure (preferably, 80 mm Hg) in a certain time frame (preferably, within 3 minutes or sooner) may be established.

EXAMPLE 1A

In an example of production by electrostatic spraying (or, more simply, electrospraying), charged droplets are generated at the tip of a metal needle (or pipette with a wire immersed in the liquid) with a several kV dc field, and are subsequently delivered to a grounded target. The droplets are derived by charging a liquid typically to 5-20 kV, which leads to charge injection into the liquid from the electrode. The sign of the injected charge depends upon the polarity of the electrode; a negative electrode produces a negatively charged liquid. The charged liquid is attracted to an electrode of opposite polarity some distance away, forming a so-called Taylor cone at the needle tip. Droplets are formed when electrostatic repulsions within the liquid exceed its surface tension. If the liquid is relatively volatile, evaporation leads to shrinkage of the droplets and an increase in excess charge density, leading to break-up into smaller droplets. This can happen many times prior to reaching the target, thereby affording very small droplets. Relatively dilute polymer solutions deposit as nodules as the result of electrospraying.

EXAMPLE 1B

Figure 1B:
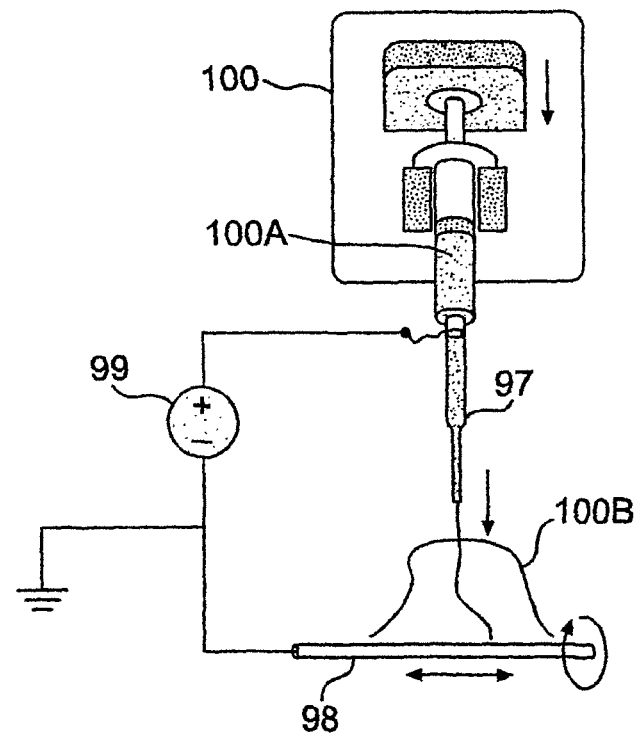
FIG. 1B shows the apparatus of FIG. 1A in the process of electrospinning production.
Figure 2A:
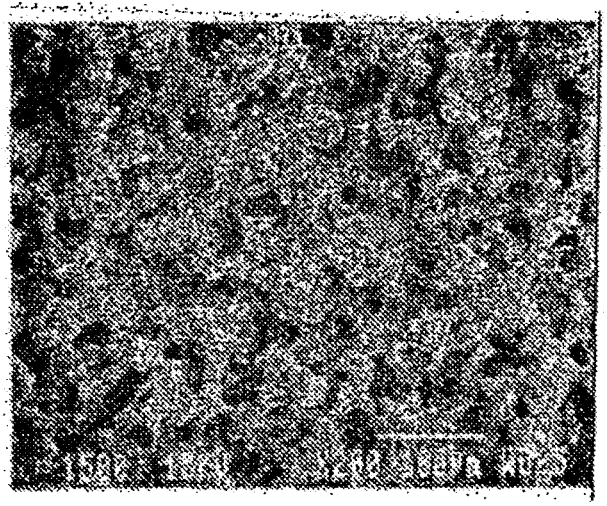
FIGS. 2A-2B are microphotographs showing PEVA deposited from a solution in chloroform that is 9 wt % solution in chloroform (FIG. 2A) and 15 wt % solution in chloroform (FIG. 2B).
Figure 2B:
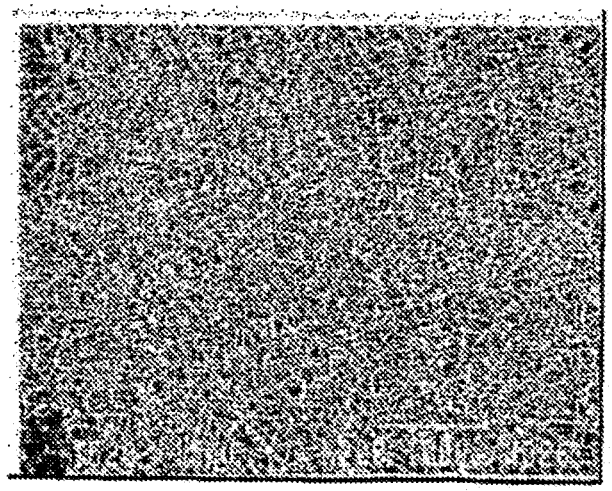

In an example of production by electrospinning, referring to FIGS. 1A-1B, polymer solutions or melts 100A are deposited as fibrous mats 100B (rather than droplets as in electrospraying), with the advantage taken of chain entanglements in melts or at sufficiently high polymer concentrations in solution to produce continuous fibers, such as a PEVA deposited from 15 wt % solution in chloroform (see FIG. 2B which is a microphotograph of such a fiber). See Stetzel et al, supra. Electrospinning is believed to be mechanistically similar to electrospraying, with differences being that chain entanglements yield a fiber from the Taylor cone. Moreover, rather than break-up into small droplets, entanglements lead to splaying of fibers into thinner ones, which is a particularly attractive aspect of electrospinning.

EXAMPLE 2A

Poly(acrylamide-co-acrylic acid copolymer was disposed in electrospun ethylene-vinyl-acetate (EVA) copolymer bags of dimensions about 6 cm by 6 cm by about 5 mm thick. The bags were exposed to water, and the bags were weighed as time progressed, with the results shown in FIG. 8A where g water/g polymer is plotted against time (minutes).

EXAMPLE 2B

A sample was prepared and tested as in Example 2A, except that instead of using poly(acrylamide-co-acrylic acid copolymer, there was used poly(acrylamide-co-acrylic acid copolymer potassium salt). The results are shown in FIG. 8B.

While the invention has been described in terms of its preferred embodiments, those skilled in the art will recognize that the invention can be practiced with modification within the spirit and scope of the appended claims.

We claim:

1. A method for treating a high pressure bleeding wound, comprising the steps of:
   inserting one or more medical devices which generate a back-pressure directly in said high pressure bleeding wound, each of said one or more medical devices comprising
   (i) a swellable material; and
   (ii) a membrane having a first side and a second side, said membrane retaining said swellable material on said first side and permitting blood to pass through from said second side to said first side of said membrane, said swellable material being swellable upon contact with blood which passes through said membrane from said second side to said first side, said membrane being expandable upon swelling of said swellable material, and said swellable material and said membrane having attributes whereby swelling of said swellable material and expansion of said membrane within said bleeding wound fills said bleeding wound and generates a back pressure in said bleeding wound of at least 60 mm Hg pressure within three minutes of being placed in said bleeding wound; and permitting said one or more medical devices to swell within said bleeding wound and to develop a back pressure within said bleeding wound.

2. The method of claim 1 wherein said inserting step is performed by inserting two or more medical devices in said bleeding wound.

3. The method of claim 1 further comprising the step of releasing one or more clot inducing substances from said one or more medical devices into said bleeding wound.

4. The method of claim 1 further comprising the step of releasing one or more of antibiotics and analgesics from said one or more medical devices into said bleeding wound.

* * * * *